(12) United States Patent
Schild et al.

(10) Patent No.: US 9,017,654 B2
(45) Date of Patent: Apr. 28, 2015

(54) PREPARATION FOR VACCINATION, VACCINATION METHOD AND USE OF A VACCINATION PREPARATION

(75) Inventors: Hansjoerg Schild, Schwabenheim (DE); Tobias Warger, München (DE); Markus Radsak, Mainz (DE); Gerd Rechtsteiner, Ginsheim-Gustarsburg (DE)

(73) Assignee: Johannes-Gutenberg-Universitaet Mainz, Mainz (DE)

( * ) Notice: Subject to any disclaimer, the term of this patent is extended or adjusted under 35 U.S.C. 154(b) by 2000 days.

(21) Appl. No.: 11/664,817

(22) PCT Filed: Oct. 6, 2005

(86) PCT No.: PCT/EP2005/010785
§ 371 (c)(1),
(2), (4) Date: Jul. 31, 2007

(87) PCT Pub. No.: WO2006/040076
PCT Pub. Date: Apr. 20, 2006

(65) Prior Publication Data
US 2008/0193487 A1  Aug. 14, 2008

(30) Foreign Application Priority Data
Oct. 8, 2004  (DE) .................. 10 2004 049 233

(51) Int. Cl.
*A61K 38/19* (2006.01)
*A61K 39/39* (2006.01)
*A61K 45/00* (2006.01)
*A61K 39/00* (2006.01)
*A61P 37/02* (2006.01)

(52) U.S. Cl.
CPC ....... *A61K 39/39* (2013.01); *A61K 2039/55511* (2013.01); *Y10S 514/828* (2013.01)

(58) Field of Classification Search
None
See application file for complete search history.

(56) References Cited

U.S. PATENT DOCUMENTS

| | | | |
|---|---|---|---|
| 5,662,907 A | 9/1997 | Kubo et al. | |
| 6,147,086 A | 11/2000 | Brenman et al. | |
| 6,245,776 B1 | 6/2001 | Skwierczynski et al. | |
| 6,486,168 B1 | 11/2002 | Skwierczynski et al. | |
| 6,706,728 B2 | 3/2004 | Hedenstrom et al. | |
| 2002/0058674 A1 | 5/2002 | Hedenstrom et al. | |
| 2003/0185835 A1 | 10/2003 | Braun et al. | |
| 2004/0076633 A1 | 4/2004 | Thomsen et al. | |
| 2004/0091491 A1 | 5/2004 | Kedl et al. | |
| 2004/0248831 A1 | 12/2004 | Lingnau et al. | |
| 2005/0070462 A1 | 3/2005 | Schellack et al. | |
| 2006/0088542 A1 | 4/2006 | Braun et al. | |
| 2007/0015721 A1 | 1/2007 | Beaton et al. | |

FOREIGN PATENT DOCUMENTS

| | | |
|---|---|---|
| EP | 1550458 | 7/2005 |
| WO | 00/40228 | 7/2000 |
| WO | 01/15698 | 3/2001 |
| WO | 02/24225 | 3/2002 |
| WO | 02/095027 | 11/2002 |
| WO | 03/040165 | 5/2003 |
| WO | 03/080114 | 10/2003 |

OTHER PUBLICATIONS

Hofmann M. et al.,"T cell avidity determines the level of CTL activation", Eur. J. Immunol., 34, pp. 1798-1806, 2004.
Vogel T. et al., "Induction of Anti-Simian Immunodeficiency Virus Cellular and Humoral Immune Responses in Rhesus Macaques by Peptide Immunogens: Correlation of CTL Activity and Reduction of Cell-Associated but not Plasma Virus Load Following Challenge", Journal of General Virology, vol. 83, No. 1, pp. 81-91, 2002.
Kudryashov V. et al., "Toward Optimized Carbohydrate-Based Anticancer Vaccines: Epitope Clustering, Carrier Structure, and Adjuvant all influence Antibody Responses to Lewis-Gamma Conjugates in Mice", Proceedings of The National Academy of Sciences of USA, vol. 98, No. 6, pp. 3264-3269, 2001.
Obert M. et al., "Protection of Mice Against SV40 Tumors by $Pam_3Cys$, MTP-PE and $Pam_3Cys$ Conjugated with the SV40 T Antigen-Derived Peptide, K(698)-T(708)", Vaccine, vol. 16, No. 2-3, pp. 161-169, 1998.
Nardin E. H. et al., "*Plasmodium falciparum* Polyoximes: Highly Immunogenic Synthetic Vaccines Constructed by Chemoselective Ligation of Repeat B-Cell Epitopes and a Universal T-Cell Epitope of CS Protein", Vaccine, vol. 16, No. 6, pp. 590-600, 1998.
Fernandes I. et al., "Synthetic Lipopeptides Incorporated in Liposomes: In Vitro Stimulation of the Proliferation of Murine Splenocytes and In Vivo Induction of an Immune Response Against a Peptide Antigen", Molecular Immunology, vol. 34, No. 8-9, pp. 569-576, 1997.
Wiesmueller K.-H. et al., "Solid Phase Peptide Synthesis of Lipopeptide Vaccines Eliciting Epitope-Specific B-, T-Helper and T-Killer Cell Response", International Journal of Peptide and Protein Research, vol. 40, pp. 255-260, 1992.
Schlecht S. et al., "Enhancement of Protection Against *Salmonella* Infection in Mice Mediated by a Synthetic Lipopeptide Analogue of Bacterial Lipoprotein in *S. Typhimurium* Vaccines", Zentralblatt für Bakteriologie, vol. 271, No. 4, pp. 493-500, 1989.
Wiesmueller K.-H. et al., "Novel Low-Molecula-Weight Synthetic Vaccine Against Foot-and-Mouth Disease Containing a Potent B-Cell and Macrophage Activator", Vaccine, vol. 7, No. 1, pp. 29-33, 1989.

(Continued)

*Primary Examiner* — Joanne Hama
*Assistant Examiner* — Fozia Hamud
(74) *Attorney, Agent, or Firm* — Abel Law Group, LLP (57) ABSTRACT

The present invention relates to a pharmaceutical preparation, comprising at least one Toll-like receptor ligand and at least one peptide. The invention also relates to the use of such a pharmaceutical preparation and to a vaccination method.

24 Claims, 2 Drawing Sheets

(56) References Cited

OTHER PUBLICATIONS

Zuber, A. K. et al., "Topical Delivery of Imiquimod to a Mouse Model as a Novel Adjuvant for Human Immunodeficiency Virus (HIV) DNA", Vaccine, vol. 22, pp. 1791-1798, 2004.

Akira S. et al., "Toll-Like Receptor Signalling", Nature Reviews Immunology, vol. 4, pp. 499-510, 2004.

Tartour E. et al., "Synthetic and natural non-live vectors: rationale for their clinical development in cancer vaccine protocols", Vaccine, vol. 20, Suppl. 4, A32-A39, 2002.

Edelman R. et al., "Adjuvants for the Future"; in M.M. Levine, G.C. Woodrow, J.B. Kaper, G.C. Cobon (ed.), New Generation Vaccines, vol. 2, New York, Marcel Dekker, pp. 173-192, 1997.

Agrawal S. et al., "Modulation of Toll-like Receptor 9 Responses through Synthetic Immunostimulatory Motifs of DNA", Ann N. Y. Acad. Sci., 1002, pp. 30-42, 2003.

Berger T.G. et al., "Dendritic Cell-Based Immunotherapy", Curr. Top. Microbiol. Immunol., 276, pp. 163-197, 2003.

Schuler G. et al., "The use of dendritic cells in cancer immunotherapy", Curr. Opin. Immunol., 15, pp. 138-147, 2003.

```
                        SEQUENCE LISTING

<160> NUMBER OF SEQ ID NOS: 23

<210> SEQ ID NO 1
<211> LENGTH: 9
<212> TYPE: PRT
<213> ORGANISM: Unknown
<220> FEATURE:
<223> OTHER INFORMATION: Description of Unknown: Mammal P53 322-330
      sequence

<400> SEQUENCE: 1

Pro Leu Asp Gly Glu Tyr Phe Thr Leu
1               5

<210> SEQ ID NO 2
<211> LENGTH: 9
<212> TYPE: PRT
<213> ORGANISM: Unknown
<220> FEATURE:
<223> OTHER INFORMATION: Description of Unknown: Tyrosinase 351-359
      sequence

<400> SEQUENCE: 2

Tyr Met Asn Gly Thr Met Ser Gln Val
1               5

<210> SEQ ID NO 3
<211> LENGTH: 9
<212> TYPE: PRT
<213> ORGANISM: Unknown
<220> FEATURE:
<223> OTHER INFORMATION: Description of Unknown: Melan A/Mart-1 27-35
      sequence

<400> SEQUENCE: 3

Ala Ala Gly Ile Gly Ile Leu Thr Val
1               5

<210> SEQ ID NO 4
<211> LENGTH: 9
<212> TYPE: PRT
<213> ORGANISM: Unknown
<220> FEATURE:
<223> OTHER INFORMATION: Description of Unknown: HER-2/neu 754-762
      sequence

<400> SEQUENCE: 4

Val Leu Arg Glu Asn Thr Ser Pro Lys
1               5

<210> SEQ ID NO 5
```

```
<211> LENGTH: 10
<212> TYPE: PRT
<213> ORGANISM: Unknown
<220> FEATURE:
<223> OTHER INFORMATION: Description of Unknown: RAGE-1 (Orf2) 11-20
      sequence

<400> SEQUENCE: 5

Ser Pro Ser Ser Asn Arg Ile Arg Asn Thr
1               5                   10

<210> SEQ ID NO 6
<211> LENGTH: 9
<212> TYPE: PRT
<213> ORGANISM: Human papillomavirus type 11

<400> SEQUENCE: 6

Arg Leu Val Thr Leu Lys Asp Ile Val
1               5

<210> SEQ ID NO 7
<211> LENGTH: 10
<212> TYPE: PRT
<213> ORGANISM: Epstein-Barr virus

<400> SEQUENCE: 7

Ala Val Phe Asp Arg Lys Ser Asp Ala Lys
1               5                   10

<210> SEQ ID NO 8
<211> LENGTH: 10
<212> TYPE: PRT
<213> ORGANISM: Hepatitis B virus

<400> SEQUENCE: 8

Gly Leu Ser Pro Thr Val Trp Leu Ser Val
1               5                   10

<210> SEQ ID NO 9
<211> LENGTH: 9
<212> TYPE: PRT
<213> ORGANISM: Human immunodeficiency virus 1

<400> SEQUENCE: 9

Ile Leu Lys Glu Pro Val His Gly Val
1               5

<210> SEQ ID NO 10
<211> LENGTH: 9
<212> TYPE: PRT
<213> ORGANISM: Human immunodeficiency virus 1

<400> SEQUENCE: 10

Lys Ile Arg Leu Arg Pro Gly Gly Lys
1               5

<210> SEQ ID NO 11
<211> LENGTH: 10
<212> TYPE: PRT
<213> ORGANISM: Human immunodeficiency virus 1

<400> SEQUENCE: 11

Thr Pro Gly Pro Gly Val Arg Tyr Pro Leu
1               5                   10
```

```
<210> SEQ ID NO 12
<211> LENGTH: 10
<212> TYPE: PRT
<213> ORGANISM: Influenza A virus

<400> SEQUENCE: 12

Ile Leu Gly Phe Val Phe Thr Leu Thr Val
1               5                   10

<210> SEQ ID NO 13
<211> LENGTH: 10
<212> TYPE: PRT
<213> ORGANISM: Mycobacterium tuberculosis

<400> SEQUENCE: 13

Val Leu Thr Asp Gly Asn Pro Pro Glu Val
1               5                   10

<210> SEQ ID NO 14
<211> LENGTH: 12
<212> TYPE: PRT
<213> ORGANISM: Unknown
<220> FEATURE:
<223> OTHER INFORMATION: Description of Unknown: MAGEA3 247-258 sequence

<400> SEQUENCE: 14

Thr Gln His Phe Val Gln Glu Asn Tyr Leu Glu Tyr
1               5                   10

<210> SEQ ID NO 15
<211> LENGTH: 15
<212> TYPE: PRT
<213> ORGANISM: Unknown
<220> FEATURE:
<223> OTHER INFORMATION: Description of Unknown: LDL receptor FUT
      fusion-protein 315-330 sequence

<400> SEQUENCE: 15

Trp Arg Arg Ala Pro Ala Pro Gly Ala Lys Ala Met Ala Pro Gly
1               5                   10                  15

<210> SEQ ID NO 16
<211> LENGTH: 19
<212> TYPE: PRT
<213> ORGANISM: Human immunodeficiency virus 1

<400> SEQUENCE: 16

Phe Arg Lys Gln Asn Pro Asp Ile Val Ile Gln Tyr Met Asp Asp Leu
1               5                   10                  15

Tyr Val Gly

<210> SEQ ID NO 17
<211> LENGTH: 20
<212> TYPE: PRT
<213> ORGANISM: Human immunodeficiency virus 1

<400> SEQUENCE: 17

Arg Ile His Ile Gly Pro Gly Arg Ala Phe Tyr Thr Thr Lys Asn Ile
1               5                   10                  15

Ile Gly Thr Ile
            20

<210> SEQ ID NO 18
<211> LENGTH: 20
<212> TYPE: PRT
```

```
<213> ORGANISM: Epstein-Barr virus

<400> SEQUENCE: 18

Pro Gly Pro Leu Arg Glu Ser Ile Val Cys Tyr Phe Met Val Phe Leu
1               5                   10                  15

Gln Thr His Ile
            20

<210> SEQ ID NO 19
<211> LENGTH: 13
<212> TYPE: PRT
<213> ORGANISM: Influenza B virus

<400> SEQUENCE: 19

Pro Tyr Tyr Thr Gly Glu His Ala Lys Ala Ile Gly Asn
1               5                   10

<210> SEQ ID NO 20
<211> LENGTH: 16
<212> TYPE: PRT
<213> ORGANISM: Mycobacterium leprae

<400> SEQUENCE: 20

Ile Ala Phe Asn Ser Gly Met Glu Pro Gly Val Val Ala Glu Lys Val
1               5                   10                  15

<210> SEQ ID NO 21
<211> LENGTH: 16
<212> TYPE: PRT
<213> ORGANISM: Hepatitis delta virus

<400> SEQUENCE: 21

Lys Gln Glu Glu Leu Glu Arg Asp Leu Arg Lys Thr Lys Lys Lys Ile
1               5                   10                  15

<210> SEQ ID NO 22
<211> LENGTH: 18
<212> TYPE: PRT
<213> ORGANISM: Mycobacterium tuberculosis

<400> SEQUENCE: 22

Gly Arg Asp Ile Lys Val Gln Phe Gln Ser Gly Gly Asn Asn Ser Pro
1               5                   10                  15

Ala Val

<210> SEQ ID NO 23
<211> LENGTH: 10
<212> TYPE: PRT
<213> ORGANISM: Adenovirus type 5

<400> SEQUENCE: 23

Ser Gly Pro Ser Asn Thr Pro Pro Glu Ile
1               5                   10
```

PREPARATION FOR VACCINATION, VACCINATION METHOD AND USE OF A VACCINATION PREPARATION

CROSS-REFERENCE TO RELATED APPLICATIONS

The present application is a U.S. National Stage of International Application No. PCT/EP2005/010785, filed Oct. 6, 2005, which claims priority of German Patent Application No. 10 2004 049 223.9, filed Oct. 8, 2004.

SEQUENCE LISTING

The instant application contains a Sequence Listing which has been submitted electronically in ASCII format and is hereby incorporated by reference in its entirety. Said ASCII copy, created on Dec. 18, 2013, is named 4121-P31919_SL.txt and is 4,992 bytes in size.

BACKGROUND OF THE INVENTION

1. Field of the Invention

The present invention relates to a pharmaceutical preparation, comprising at least one Toll-like receptor ligand and at least one peptide. The invention also relates to the use of such a pharmaceutical preparation and to a vaccination method.

2. Discussion of Background Information

The adaptive immune system plays an important role in immune defence against specific microorganisms, for example viruses, specific fungi and bacteria, as well as in recognising and repelling malignant (degenerate) cells (tumour cells). Here diseased, i.e. virus-infected or malignant, cells are specifically recognised and eliminated by what are known as cytotoxic T cells (CTL, killer cells). A necessary prerequisite for recognition of the diseased cells by the cytotoxic T cells is the interaction of the T cell receptor (TCR) of the cytotoxic cells with a main histocompatibility complex I (MHC I). Protein fragments (from peptides consisting of 8 to 10 amino acids, what are known as MHC class I ligands) are presented on the cell surface by MHC I molecules. These are then specifically recognised by a T cell receptor (TCR). MHC class I ligands are generated in every cell by enzymatic breakdown and are presented on the cell surface (what are known as self-peptides). Virus-specific or tumour-specific self-peptides are also presented on virus-infected or malignant cells. Such cells can thus be recognised and destroyed by cytotoxic T cells (CTL) with a virus-specific or tumour-specific T cell receptor.

To prevent damage to healthy cells, which also present self-peptides, by cytotoxic T cells (CTL), in addition to the specific interaction between T cell receptor and MHC I self-peptide, CTLs must first of all be activated by additional co-stimulatory signals, so they can subsequently recognise and destroy their target cells (virus-infected cells or tumour cells). Without prior activation a cytotoxic cell (CTL), despite its T cell receptor specific to a certain (for example virus-infected or malignant) target cell, cannot recognise and destroy the target cells via the specific self-peptides thereof. If, on the other hand, cytotoxic T cells, which comprise specific receptors for self-peptides presented on cells, are wrongly activated, for example within the framework of an infection, this can lead to reactions of cytotoxic cells against healthy tissue cells. Regulation of the activation of cytotoxic T cells is therefore of prime importance for whether a specific immune response is initiated or not.

On activation of cytotoxic T cells with initiation of a specific immune response what are known as professional antigen-presenting cells (APC) play a particular role. Antigen-presenting cells are specialised cells which absorb and present antigens very efficiently (for example viruses or bacteria). Examples are dendritic cells (DC) or the Langerhans cells in the skin. DCs mature in the presence of danger signals. This leads to a high regulation of co-stimulatory signals. In this situation the recognition of antigens leads to activation of cytotoxic T cells (CTL) and to initiation of the immune response.

For an efficient T cell response to occur the activating interaction between the cytotoxic T cells and professional antigen-presenting cells is therefore necessary, and the specific activation of the T cells takes place owing to two different signals being received, namely the specific recognition of the antigen owing to suitable receptors, and co-stimulatory signals which are imparted by the receptors and messengers of the antigen-presenting cells (APC). The APCs only pass on these co-stimulatory signals in the activated state, however. The activation of the APC can be attained by stimulation of what are known as Toll-like receptors (TLR).

"Danger signals" which lead to maturing of dendritic cells can have different natures. They can for example originate from activated T helper cells or even directly from pathogens. If the "danger signals" originate from pathogens, certain conserved virus, bacteria or fungi structures can, for example, be recognised by the Toll-like receptors.

A total of 11 different Toll-like receptors (TLR) have been known up to now and natural and synthetic ligands are described for many of these ["S. Akira, K. Takeda; Toll-like receptor signalling' Nat. Rev. Immunol. 2004; 4, 499 to 511"]. For example cell wall components of gram-negative bacteria (lipopolysaccharides; LPS) of TLR4 are recognised. The genomic dsRNSs of certain viruses are recognised by TLR3. Documents WO-A 00/040,228, WO-A 01/015,698 and WO-A 045,494 also describe the recognition of different viral structures, which occur in connection with human and animal diseases, by TLR7, i.e. the substance imiquimod {1-(2-methylpropyl-)1H-imidazo[4,5-c]quinolin-4-amine}.

Despite significant advances in the understanding of the above-described underlying functionality of the adaptive immune response and improved knowledge of the antigen structures that exist on diseased (for example virus-infected) cells or tumour cells and are recognised by specific cell receptors, until now it has only be insufficiently possible to activate the adaptive immune system by therapeutic measures with the aim of specifically eliminating diseased cells or tumour cells.

Vaccinations are a long-known method of activating the immune system. Previously it has been possible to use vaccinations substantially only prophylactically since the administration of a vaccine leads to production of protective antibodies (B cell response). Immunisation takes a relatively long time, usually several weeks, so the therapeutic use of vaccinations (i.e. the rapid activation of the immune system for treating acute states) is largely rejected. The development of strategies in which intervention in the cascade of activation of T cells is possible, thereby generating a T cell response, is therefore of immense interest. In the individual case this could be beneficial therapeutically as well as prophylactically.

Tumour immunology incorporates a wide field of biological phenomena which include the interaction of malignant, degenerate cells with the congenital and adaptive immune system. Among the various types of immune cells T cells play a central role since they can recognise and eliminate specific tumour cells. Since most tumour-associated proteins occur intracellularly, T cells are obviously the most suitable tool for inducing a tumour-specific immune response. In particular antibodies cannot penetrate into the cell and congenital immune cells lack the high-grade specificity of T cells. The above-described activation of cytotoxic T cells, which eliminate only diseased cells, but spare healthy ones, is therefore an attractive aim for the prevention and treatment of infections, specifically virus-induced infections and tumoral diseases.

For the majority of conventional vaccination strategies it is necessary to carry out a plurality of immunisation steps to attain adequate immunity. Immunity usually results from the production of protective antibodies against the antigen administered in the course of vaccination.

Previous strategies for inducing T cells by immunisation used preparations which contain the corresponding antigen in conjunction with auxiliaries/adjuvants, such as aluminium-containing substances or virus-like particles (VLP), incomplete Freund's adjuvants or similar oil-in-water mixtures or CpG-DNS. The preparations are applied subcutaneously or intradermally by means of injection. This is disclosed for example in the documents "E. Tartour, F. Benchetrit, N. Haicheur, O. Adotevi and W. H. Fridman; Synthetic and natural non-live vectors: rationale for their clinical development in cancer vaccine protocols; Vaccine, 19 Dec. 2002: 20 (Suppl. 4) A 32 to 39"; "R. Edelmann: Adjuvants for the future; in M. M. Levine, G. C. Woodrow, J. B. Kaper, G. S. Cobon (ed.), New Generation Vaccines, vol. 2, New York, Marcel Dekker (1997), 173 to 192)"; and "S. Agrwal, E. R. Kadnimalia; Modulation of Toll-like Receptor 9 responses through synthetic immunostimulatory motifs of DNA; Ann. N.Y. Acad. Sci. 2003 (December): 1002, 30 to 42". An attempt has also been made to initiate T cell responses with the aid of dendritic cells, of which the precursor cells have been previously obtained from blood and differentiated in vitro ["T. G. Berger, E. S. Schultz; Dendritic cell-based immunotherapy; Curr. Top. Microbiol. Immunol. 2003: 276, 163 to 197"] or to use dendritic cells as adjutants in that these were charged with MHC class I ligands, tumour-associated proteins or tumour cell lysates and patients were injected ["G. Schuler, B. Schuler-Thurner, R. M. Steinmann; The use of dendritic cells in cancer immunotherapy; Curr. Opin. Immunol. 2003: 15, 138 to 147"].

Owing to the significance of T cells to the elimination of intracellular pathogens and tumour cells, more recent immunisation strategies attempt to activate T cells, in particular cytotoxic T cells, and this would also open up the possibilities of therapeutic vaccinations. Common to all previous vaccination strategies is that they function passably in practice, in other words, that cytotoxic T cells for example can be measurably activated in patients and their number may be increased. However, the methods are only moderately capable of generating efficient T cell responses, in particular of attaining adequate repulsion of tumours. In addition the known vaccination methods are still associated with significant side effects through to toxicity ["E. Tartour et al, loc. cit.", and R. Edelmann, loc. cit."]. It is known from animal models that in the case of vaccinations with CpG-DNS side effects occur which considerably limit use of this adjuvant. In addition the DC-based methods in particular are associated with a level of expenditure which cannot be transferred to the daily routine of a hospital or practice.

The object of the invention was to contribute to significantly improved generation of cytotoxic T cells by way of efficient activation without the drawbacks of the prior art occurring in the process. In particular the aim is to achieve efficient activation of antigen-presenting cells via activation of Toll-like receptors. These cells make sure of efficient activation of specific cytotoxic T cells by increased expression of co-stimulatory signals.

A further object of the invention was to disclose a method of non-invasive triggering of a systemic, T cell-imparted immune response.

Yet another object of the invention was to provide an inexpensive vaccination concept, associated with only low technical complexity, for generating cytotoxic T cells.

Yet another object of the invention was to provide preparations for new preventative and therapeutic methods on an immunological basis against a broad spectrum of diseases, including diseases triggered by viruses or bacteria and tumoral diseases.

Surprisingly it has been found according to the invention that topically administered preparations which contain the necessary specific peptide signal substances for the T cell receptor together with a ligand for a Toll-like receptor are non-invasively capable of triggering a systemic T cell imparted immune response in that they are capable of generating specific cytotoxic T cells. A simple, fast and efficient method is thereby disclosed for inducing immune responses to any desired T cell antigen.

The invention therefore relates to a pharmaceutical preparation which comprises at least one Toll-like receptor ligand, at least one peptide and optionally one or more substance(s) from the group comprising carriers, adjuvants and additives.

The invention also relates to the use of a pharmaceutical preparation as described in detail hereinafter for the prophylaxis and/or therapy of diseases in a mammal induced by viruses and/or bacteria and/or fungi and for the preparation of a pharmaceutical composition for the prophylaxis and/or therapy of diseases in a mammal induced by viruses and/or bacteria and/or fungi.

The invention also relates to the use of a pharmaceutical preparation as described in detail hereinafter for the prophylaxis and/or therapy of diseases in a mammal caused by excessive cell proliferation and for the preparation of a pharmaceutical composition for the prophylaxis and/or therapy of diseases in a mammal caused by excessive cell proliferation.

The invention also relates to methods for the prophylaxis and/or therapy of diseases in a mammal induced by viruses and/or bacteria and/or fungi and for the prophylaxis and/or therapy of diseases caused by excessive cell proliferation, comprising the administration of a pharmaceutical preparation, according to the detailed description hereinafter, to the mammal in a concentration of the pharmacologically effective components that is effective for the prophylaxis and/or therapy of said diseases.

The invention also relates to a method for the prophylactic and/or therapeutic activation of the adaptive immune system of a mammal, comprising the administration of a pharmaceutical preparation, as described in detail hereinafter, to the mammal in a concentration of the pharmacologically effective components that is effective for the prophylactic and/or therapeutic activation of the mammal's immune system, and to a method for the prophylactic and/or therapeutic activation of cytotoxic T cells in the immune system of a mammal, comprising the administration of a pharmaceutical preparation, as described in detail hereinafter, to the mammal in a concentration of the pharmacologically effective components that is effective for the prophylactic and/or therapeutic activation of the cytotoxic T cells.

SUMMARY OF THE INVENTION

The present invention provides a pharmaceutical combination which comprises (a) at least one Toll-like receptor ligand which is selected from TLR2 ligands, TLR3 ligands, TLR7 ligands, TLR8 ligands and TLR9 ligands and (b) at least one peptide which is selected from major histocompatibility complex class I ligands, major histocompatibility complex class II ligands and peptides which comprise one or more of these histocompatibility complex ligands and are capable of being presented by a MHC class I molecule and/or a MHC class II molecule.

In one aspect of the combination, the at least one Toll-like receptor ligand may be selected from compounds of natural and/or synthetic origin which are capable of being recognized by at least one Toll-like receptor and are capable of contributing to a triggering of one or more signals which promote an immune response. For example, the at least one Toll-like receptor ligand may comprise at least one TLR7 ligand such as, e.g., one or more of Pam3Cys, poly-(I:C), imiquimod, loxoribine, R-848 and CpG-DNA, in particular, imiquimod.

In another aspect, the combination may comprise at least one synthetic Toll-like receptor ligand (a) and at least one synthetic peptide (b) and may be present as a single formulation which comprises (a) and (b) for combined administration and effect.

In yet another aspect, the combination may comprise at least one synthetic Toll-like receptor ligand (a) and at least one synthetic peptide (b) and may comprise (a) and (b) in at least two separate formulations for a combined effect. For example, a first one of the at least two separate formulations may be present in a form which is adapted for topical administration and a second one of the at least two formulations may be present in a form which is adapted for non-topical administration (e.g., a subcutaneous and/or an intradermal administration) and/or the first one of the at least two formulations may comprise (a) and the second one of the at least two formulations may comprise (b).

The present invention also provides a pharmaceutical preparation which comprises from 0.1% to 10% by weight of (a) at least one Toll-like receptor ligand selected from TLR2 ligands, TLR3 ligands, TLR7 ligands, TLR8 ligands and TLR9 ligands, from 0.01% to 30% by weight of (b) at least one peptide selected from major histocompatibility complex class I ligands, major histocompatibility complex class II ligands and peptides which comprise one or more of these histocompatibility complex ligands and are capable of being presented by a MHC class I molecule and/or a MHC class II molecule, and from 0.1% to 99.9% by weight of (c) one or more substances selected from carriers, adjuvants and additives, in each case based on the total weight of the preparation.

In one aspect, the preparation may comprise at least 1% by weight of (a) and not more than 5% by weight of (b). For example, the preparation may comprise from 1% to 5% by weight of (a) and from 0.2% to 2% by weight of (b).

In another aspect, the preparation may be present in a form which is suitable (adapted) for topical administration.

The present invention also provides a method for the prophylaxis and/or therapy in a mammal of a disease which is induced by viruses, bacteria and/or fungi. The method comprises administering to the mammal the pharmaceutical combination of the present invention as set forth above, including the various aspects thereof, in an amount which is effective for the prophylaxis and/or therapy of the disease.

The present invention also provides a method for the prophylaxis and/or therapy in a mammal of a disease which is caused by excessive cell proliferation. The method comprises administering to the mammal the pharmaceutical combination of the present invention as set forth above, including the various aspects thereof, in an amount which is effective for the prophylaxis and/or therapy of the disease.

The present invention also provides a method for the prophylactic and/or therapeutic activation of the adaptive immune system of a mammal. The method comprises administering to the mammal the pharmaceutical combination of the present invention as set forth above, including the various aspects thereof, in an amount which is effective for the prophylactic and/or therapeutic activation of the mammal's immune system.

The present invention also provides a method for the prophylactic and/or therapeutic activation of cytotoxic T cells in the immune system of a mammal. The method comprises administering to the mammal the pharmaceutical combination of the present invention as set forth above, including the various aspects thereof, in an amount which is effective for the prophylactic and/or therapeutic activation of the cytotoxic T cells.

In one aspect of the above methods, the mammal may be a human.

In another aspect, the methods may comprise the topical administration of at least one component of the combination. This component may, for example, comprise component (a) of the combination.

In another aspect, at least one other component of the combination may be administered non-topically, e.g., subcutaneously and/or intradermally. This component may, for example, comprise component (b) of the combination.

BRIEF DESCRIPTION OF THE DRAWINGS

In the appended drawings.

DETAILED DESCRIPTION OF THE INVENTION

The pharmaceutical preparations according to the invention comprise as an essential component at least one Toll-like receptor ligand (TLR ligand). In the present description and in the claims Toll-like receptor ligands are taken to mean compounds of natural and/or synthetic origin which are recognised by at least one Toll-like receptor and are useful for triggering signals that promote the immune response. The Toll-like receptor ligand(s) that can be used according to the invention can be natural or synthetic or synthetically modified natural compound(s). In a preferred embodiment of the invention the Toll-like receptor ligand(s) can be synthetic substances. The previously known Toll-like receptor ligands have been divided into groups of the compounds recognised by the respective Toll-like receptors TLR1, TLR2, TLR3, TLR4, etc. Until now 11 Toll-like receptors (up to TLR11) have been known. The ligands are generally called TLR1 ligands, TLR2 ligands, TLR3 ligands, TLR4 ligands, etc. up to TLR11 ligands. However, what is decisive is not the name of the ligand but only its characteristic property of being recognised by a Toll-like receptor. A Toll-like receptor ligand is regularly used in the pharmaceutical preparation according to the invention. However it is also possible to use two or more Toll-like receptor ligands.

In a preferred embodiment the invention relates to a pharmaceutical preparation in which the at least one Toll-like receptor ligand is selected from TLR2 ligand, TLR3 ligand, TLR7 ligand, TLR8 ligand and TLR9 ligand. According to the invention a TLR7 ligand is preferably used. In even more preferred embodiments of the invention the pharmaceutical preparation comprises at least one, even more preferred, precisely one, Toll-like receptor ligand from the group comprising compounds of natural and/or synthetic origin which are recognised by at least one Toll-like receptor and are useful for triggering one or more signal(s) that promote the immune response. The term "natural and/or synthetic origin" is in this context taken to mean that the compounds suitable as the ligand of at least one Toll-like receptor is either a compound that also occurs naturally as a Toll-like receptor ligand or an artificially synthesised compound that is suitable anyhow as a ligand however or a naturally occurring, but synthetically modified compound (for example—but not exclusively—one of the compounds as are described in document WO-A 00/040228) or a compound, as described above, that occurs naturally as a Toll-like ligand which has been chemically modified, for example substituted or derivatised in some other way.

The at least one Toll-like receptor ligand is even more advantageously selected from the group comprising Pam3Cys, poly-(I:C), imiquimod, loxoribine, R-848 and CpG-DNA. In preparations that are most particularly preferred according to the invention the Toll-like receptor ligand is imiquimod. The compound known per se by the name of imiquimod has the chemical name 1-(2-methylpropyl-)1H-imidazo[4,5-c]quinolin-4-amine.

As further essential components the pharmaceutical preparation comprises at least one peptide. Synthetic and/or natural peptides are suitable as the peptide. According to the invention "synthetic and/or natural" is taken to mean that the peptide is either a naturally occurring peptide or an artificially synthesised, but anyhow suitable peptide according to the invention, or a naturally occurring but synthetically modified peptide. A peptide is regularly used in the pharmaceutical preparation according to the invention. However it is also possible to use two or more peptides. The use of an individual peptide is preferred according to the invention owing to the specificity of signal triggering.

In preferred embodiments of the pharmaceutical preparation according to the invention the at least one peptide is selected from major histocompatibility complex class I ligand, major histocompatibility complex class II ligand and further peptides containing these ligands. Such peptides are more preferably antigens for recognition by cytotoxic T-cells and even more preferably peptides of viral or bacterial origin or tumour-specific peptides or tumour-associated peptides. These can be presented by MHC class I molecules and by MHC class II molecules.

Without restriction peptides cited purely by way of example, which according to the invention can be used particularly advantageously in the pharmaceutical preparations of the invention, can be found in the following table 1 without the invention being limited thereto.

TABLE 1

Particularly preferred peptides for use in pharmaceutical preparations according to the invention

| SEQ ID NO: | Sequence | Source | HLA allele |
|---|---|---|---|
| | MHC class I ligands | | |
| | Tumour | | |
| 1 | PLDGEYFTL | P53 322-330 | HLA-A*0201 |
| 2 | YMNGTMSQV | Tyrosinase 351-359 | HLA-A*0201 |
| 3 | AAGIGILTV | Melan A/Mart-1 27-35 | HLA-A*0201 |
| 4 | VLRENTSPK | HER-2/neu 754-762 | HLA-A*0301 |
| 5 | SPSSNRIRNT | RAGE-1 (Orf2) 11-20 | HLA-B*07 |
| | Viruses | | |
| 6 | RLVTLKDIV | HPV11E7 4-12 | HLA-A*0201 |
| 7 | AVFDRKSDAK | EBV EBNA-4 399-408 | HLA-A*0301 |
| 8 | GLSPTVWLSV | HBV surface antigen 185-194 | HLA-A*0201 |
| 9 | ILKEPVHGV | HIV-1 (BRU) RT 476-484 | HLA-A*0201 |
| 10 | KIRLRPGGK | HIV-1 (BRU) gag p17 17-25 | HLA-A*0301 |
| 11 | TPGPGVRYPL | HIV-1 (ARV-2) nef 128-137 | HLA-B*07 |
| 12 | ILGFVFTLTV | Influenza A MP 59-68 | HLA-A*0201 |
| | Bacteria | | |
| 13 | VLTDGNPPEV | M. tuberculosis 19 kD antigen 88-97 | HLA-A*0201 |
| | MHC class II ligands | | |
| | Tumour | | |
| 14 | TQHFVQENYLEY | MAGEA3 247-258 | HLADPB1*0401 |
| 15 | WRRAPAPGAKAMAPG | LDL receptor FUT fusion-protein 315-330 | HLADRB1*0101 |
| | Viruses | | |
| 16 | FRKQNPDIVIQYMDDLYVG | HIV-1 (HXB2) RT 326-345 | HLADRB1*0701 |
| 17 | RIHIGPGRAFYTTKNIIGTI | HIV-1 (MN) env 306-325 | HLADRB1*0101 |
| 18 | PGPLRESIVCYFMVFLQTHI | EBV EBNA-1 551-570 | HLADRB1*0701 |
| 19 | PYYTGEHAKAIGN | Influenza B/HK/73HA 308-329 | HLADRB1*0101 |

TABLE 1-continued

Particularly preferred peptides for use in pharmaceutical preparations according to the invention

| SEQ ID NO: | Sequence | Source | HLA allele |
|---|---|---|---|
| 20 | IAFNSGMEPGVVAEKV | M. leprae HSP65 451-466 | HLADPB1*0401 |
| 21 | KQEELERDLRKTKKKI | Hepatitis delta 27 kD Ag 26-41 | HLADPB1*1701 |
|  | Bacteria |  |  |
| 22 | GRDIKVQFQSGGNNSPAV | M. tuberculosis AG85-B 19-36 | HLD-DRB4 |

In addition to said essential components the pharmaceutical preparations according to the invention can optionally also contain one or more substance(s) form the group comprising carriers, adjuvants and additives. By way of example these include, without limiting the invention thereto, one or more substance(s) from the group comprising hydrophilic and lipophilic solvents, solubilising agents, emulsifiers, viscosity-adjusting agents, pH-adjusting agents, chelating agents, preservatives, agents for providing a basis for topical application (ointment and/or cream bases), agents for increasing the skin-penetrating capacity, etc.

Purely by way of example and without limiting the invention thereto the following are cited as carriers, adjuvants and additives: isostearic acid, benzyl alcohol, cetyl alcohol, stearyl alcohol, white Vaseline, polysorbate $80^R$, sorbitan stearate, glycerol, methyl-4-hydroxybenzoate, propyl-4-hydroxybenzoate, xanthan gum and purified water.

The quantities of the essential components contained in the pharmaceutical preparation according to the invention (at least one Toll-like receptor ligand and at least one peptide) which is prophylactically and/or therapeutically effective in a specific situation depends on various factors, such as the activity of the specific combination of at least one Toll-like receptor ligand and at least one (for example synthetic) peptide, the method of administration, the frequency of administration, the specific formulation, the state of the disease to be treated and the constitution of the mammal or patient being treated. Experts with expertise in this technical field can easily determine effective quantities in the individual case with the aid of a few orientating tests and the information contained in the present description. In this connection the term "prophylactically and/or therapeutically effective quantity" in the present description and in the claims means the quantity of the combination of the two essential components (optionally a plurality of components of the two respective components Toll-like receptor ligand and synthetic peptide) which is sufficient to trigger a prophylactic and/or therapeutic effect, for example a prophylactic and/or therapeutic effect in the prophylaxis and/or treatment of a certain disease, for example a degenerative disease or disease caused by viruses or bacteria or the like or in the prophylaxis or therapy of a disease caused by excessive cell proliferation or a tumoral disease. A prophylactically and/or therapeutically effective quantity is also a quantity which is sufficient to prophylactically and/or therapeutically activate the adaptive immune system of a mammal or a quantity which is sufficient to prophylactically and/or therapeutically activate cytotoxic T-cells of a mammals' immune system.

Preferred according to the invention are pharmaceutical preparations comprising a Toll-like ligand receptor in a quantity of 0.1 to 10% by weight, at least one peptide in a quantity of 0.01 to 30% by weight and one or more substance(s) from the group comprising carriers, adjuvants and additives in a total quantity of 0.1 to 99.9% by weight, in each case based on the total weight of the pharmaceutical preparation. Particularly preferred, since they are capable of particularly targeted activation of a mammal's immune system, are pharmaceutical preparations according to the invention comprising: at least one Toll-like receptor ligand in a quantity of 1 to 10% by weight, at least one peptide in a quantity of 0.1 to 5% by weight and one or more substance(s) from the group comprising carriers, adjuvants and additives in a total quantity of 0.5 to 99% by weight, in each case based on the total weight of the pharmaceutical preparation.

A particular, exemplary pharmaceutical preparation, but which is not limiting to the invention, comprises at least one Toll-like receptor ligand in a quantity of 1 to 5% by weight, at least one peptide in a quantity of 0.2 to 2% by weight and one or more substance(s) from the group comprising carriers, adjuvants and additives in a total quantity of 93 to 99% by weight, in each case based on the total weight of the pharmaceutical preparation.

According to a further preferred embodiment the pharmaceutical preparation according to the invention comprises the at least one Toll-like receptor ligand and the at least one peptide in a formulation for combined administration and effect. The preparation according to this advantageous embodiment, since it is in a form that is easy to administer, therefore contains the two essential components in a combined formulation, are therefore administered together and can then develop a prophylactic and/or therapeutic effect together. This allows accurate dosing of the two components in addition to simple administration. Conceivable examples of such pharmaceutical preparations according to the invention—without limiting the invention hereto—are solutions or suspensions for intraperitoneal administration, creams or ointments for topical, for example epidermal, administration, sprays for intranasal or laryngeal administration or solutions in the form of drops for intraocular administration.

A particularly preferred embodiment of such a pharmaceutical preparation according to the invention is a formulation that is suitable for topical application. A particularly clear but non-limiting example of a preparation of this type is an ointment, a cream, solution or suspension for topical, i.e. epidermal, administration, for example for topical administration of the preparation to the mammal's skin. In an embodiment of the invention that can be used with particular advantage a commercially available cream is used which contains 5% of the Toll-like receptor7 ligand imiquimod in a conventional cream base (Aldara®, 3M).

However, pharmaceutical preparations, which constitute preferred embodiments, which comprise the at least one Toll-like receptor ligand and the at least one peptide in separate formulations for separate administration and combined effect are also conceivable and incorporated by the present invention. Cases in which the at least one Toll-like receptor ligand and the at least one peptide are in the form of a separate but similar formulation (for example as a cream in both cases or as a solution in both cases) are applied separately from each other (for example topically applied), but have a combined effect as well as cases in which the at least one Toll-like receptor ligand and the at least one peptide are in the form of separate and different formulations (for example in one case as a cream and in the other case as a solution), are applied separately from each other (for example in the case of the cream by topical application and in the case of the solution by intraperitoneal administration) but in the end have a combined effect, are incorporated by this embodiment.

For the second case mentioned above a particularly preferred example of a pharmaceutical preparation according to the present invention is in a formulation suitable for topical administration of one component and for non-topical, preferably subcutaneous or intradermal, administration of another component with the aim of a combined effect. This embodiment has the advantage that the respective components can be applied using the respective administration method which guarantees their best possible combined effect in the mammal being treated. An even more preferred embodiment of the invention is a pharmaceutical preparation in a formulation suitable for topical administration of at least one Toll-like receptor ligand and a formulation suitable for non-topical, preferably subcutaneous or intradermal, administration of at least one peptide with the aim (and the result) of a combined effect. For example the at least one, more preferably the one Toll-like receptor ligand, is formulated in the form of a cream which can be applied epidermally, while the at least one peptide is formulated in the form of a solution or suspension which can be applied subcutaneously or intradermally.

The invention also relates to uses of a pharmaceutical preparation as described in detail above. Such uses lie in the fields of:
  prophylaxis and/or therapy of diseases in a mammal induced by viruses and/or bacteria and/or fungi,
  prophylaxis and/or therapy of diseases in a mammal, such as tumoral diseases, caused by excessive cell proliferation,
  preparation of a drug for the prophylaxis and/or therapy of diseases in a mammal induced by viruses and/or bacteria and/or fungi,
  preparation of a drug for the prophylaxis and/or therapy of diseases in a mammal, such as tumoral diseases, caused by excessive cell proliferation.

The use according to the invention of the pharmaceutical preparation is particularly advantageous in the prophylaxis and/or therapy of degenerative diseases, more preferably in the prophylaxis and/or therapy of diseases caused by viral or microbial pathogens, while according to the invention use of the pharmaceutical preparations in diseases caused by excessive cell proliferation and in particular in tumoral diseases is particularly preferred.

Any desired mammals can be treated within the framework of use of the pharmaceutical preparation according to the invention. Examples include mice, rats, guinea pigs, cats, dogs, monkeys and humans. In particularly preferred embodiments of the use according to the invention of the pharmaceutical preparations the treated mammal is a human.

In preferred embodiments of the invention the pharmaceutical preparation is used by way of topical application of the pharmaceutical preparation, even more preferably by way of epidermal application, in other words the application of the pharmaceutical application to the mammal's skin. An epidermally applied pharmaceutical preparation particularly preferably comprises at least one Toll-like receptor ligand and at least one peptide in one phase for combined effect on the body through the mammal's skin. Surprisingly it has in particular been found according to the invention that rapid permeation of the active ingredients through the skin can be achieved hereby and as a consequence an efficient specific immune response of the cytotoxic T-cells can be generated and thereby reliable recognition and elimination of diseased cells from the mammal's body.

A further, likewise preferred use of the pharmaceutical preparation according to the invention takes place by way of separate topical application of one component and non-topical, preferably subcutaneous or intradermal, application of another component with the aim and result of a combined effect. This occurs even more preferably by way of topical application of one component to the mammal's skin and subcutaneous or intradermal application of another component immediately before or after or at the same time as the topical application, a combined effect surprisingly occurring. If for example according to an even more preferred embodiment, but which does not limit the invention, a formulation comprising at least one Toll-like receptor ligand is topically (e.g. epidermally) applied, and a formulation comprising at least one peptide, such as a MHC class I ligand, is non-topically, for example subcutaneously or intradermally, applied shortly before or after the topical application of the other component or substantially at the same time therewith (it also being possible to chose the reverse sequence), a combined effect of the two components Toll-like receptor ligand and MHC class I ligand occurs insofar as—as with the combined administration of the two components in one preparation by the same application method—antigen-presenting cells in the skin bind and present the MHC class I ligand and at the same time co-stimulatory signals are stimulated by the Toll-like receptor ligand for intervention. On a purely practical level this leads to the antigen-presenting cells of the skin moving into the regional lymph nodes where they come into contact with naive cytotoxic T cells and activate these specifically for recognition and elimination of cells which present the peptide. This use opens up new possibilities of treating previously untreatable diseases, including tumoral diseases and various infectious diseases.

The invention also relates to a method for the prophylaxis and/or therapy of diseases in a mammal induced by viruses and/or bacteria and/or fungi, comprising the administration of a pharmaceutical preparation, according to the detailed description above, to a mammal in a concentration of the pharmacologically effective components that is effective for the prophylaxis and/or therapy of said diseases.

The invention also relates to a method for the prophylaxis and/or therapy of diseases in a mammal caused by excessive cell proliferation (in particular tumoral diseases), comprising the administration of a pharmaceutical preparation, according to the detailed description above, to the mammal in a concentration of the pharmacologically effective components that is effective for the prophylaxis and/or therapy of said diseases.

The invention also relates to a method for the prophylactic and/or therapeutic activation of the adaptive immune system of a mammal, comprising the administration of a pharmaceutical preparation, according to the detailed description above, to the mammal in a concentration of the pharmacologically effective components that is effective for the prophylactic and/or therapeutic activation of the immune system.

The invention also relates to a method for the prophylactic and/or therapeutic activation of cytotoxic T cells in the immune system of a mammal, comprising the administration of a pharmaceutical preparation, according to the detailed description above, to the mammal in a concentration of the pharmacologically effective components that is effective for the prophylactic and/or therapeutic activation of the cytotoxic T cells.

The term "prophylaxis" or "prophylactic", as it is used in the present description and the claims, designates a treatment or effect of a treatment of the mammal body that is of preventative character, in other words has the aim of preventing the onset of a disease. This includes cases in which a treatment is temporarily pursued to prevent an occurrence of the disease for the first time, as well as cases in which a treatment is temporarily pursued to prevent a recurrence of a disease again following previous therapy and cure. The term "therapy" or "therapeutic", as it is used in the present description and the claims, designates a treatment or effect of a treatment of/on the mammal's body, where a disease has already appeared, for the fast and/or complete termination thereof by the establishment of a healthy mammal body state.

Accordingly a prophylactic activation of the adaptive immune system or a prophylactic activation of the cytotoxic T cells is understood as an activation that is intended to prevent a disease from occurring while the corresponding therapeutic activation is used for the fast and/or complete termination of a disease that has already appeared. In particular within the framework of activation of the adaptive immune system and activation of the cytotoxic T cells in a mammal's body, the present invention preferably applies to the therapeutic components, i.e. the rapid reaction to an actually occurring disease stage by activating the mammal's immune system.

The treatment—regardless of whether it is prophylactic or therapeutic or both—includes the administration of a pharmaceutical preparation according to the invention, as has bee described above in detail, to a mammal as an essential step, optionally after or before other method steps which are used for the same prophylactic and/or therapeutic aim. Administration can take place by any desired method, without the invention being limited to a specific method. Examples of administration include intraperitoneal, intravenous, intramuscular, subcutaneous or intradermal, topical (e.g. epidermal), oral, intranasal, etc. Preferred according to the invention is a method in which the pharmaceutical preparation is administered topically, even more preferably where the pharmaceutical preparation is applied to the skin of a mammal, in particular of a human. Surprisingly this method of administration opens up the straightforward possibility for a person skilled in the art of generating an efficient specific immune response by activation of the cytotoxic T cells.

A further, likewise preferred embodiment of the invention relates to a method in which part of the pharmaceutical preparation comprising at least one component is administered topically and another part of the pharmaceutical preparation comprising another component is administered non-topically, preferably subcutaneously or intradermally, with the aim and result of a combined effect. This can take place even more preferably in that part of the pharmaceutical preparation comprising at least one component is administered by application to the skin of the mammal and administration of another part of the pharmaceutical preparation comprising at least one further component is brought about by subcutaneous or intradermal administration to the mammal immediately before or after or at the same time as application to the skin with the aim and result of a combined effect.

According to the invention there are no restrictions regarding which of the components, in particular which of the essential components of the pharmaceutical preparation according to the invention, is administered topically and which of the essential components of the pharmaceutical preparation according to the invention is administered non-topically, for example (but not limited to) subcutaneously or intradermally, since activation of the adaptive immune system can be achieved with the method according to the invention by independent manners of administering the individual components of the preparation. An approach that is used with particular advantage however is if according to the invention part of the preparation, comprising at least one Toll-like receptor ligand, is administered by way of topical application to the skin and another part of the preparation, comprising at least one peptide, is administered subcutaneously or intradermally. The two application steps are either carried out simultaneously or directly one after the other in this case of the approach according to the invention as well since the aim is the combined effect of the two components which in practice is surprisingly also achieved if the methods of administration are different. According to the invention the sequence is not stipulated so as to be limiting although it is preferred if the Toll-like receptor ligand is topically (epidermally) applied immediately after the non-topical (for example subcutaneous or intradermal) application of the peptide, for example of the MHC class I ligand.

The immunisation of the mammal or human patient achieved by the combined application of the components of the pharmaceutical preparation or their application directly one after the other is optionally repeated several times, it being possible to select any desired interval between the treatments, although there is preferably a period of at least 24 h between two applications. This has the advantage that the efficiency of the treatment is much enhanced and side effects are minimised at the same time.

The quantities of the pharmaceutical preparation administered according to the invention can be freely selected by a person skilled in the art and are not subject to any restrictions. However in practical terms it has proven expedient to use the pharmaceutical preparations, indicated as a dose for the one-off treatment, in a quantity in the range of 0.1 to 100 mg of preparation per kg body weight of the mammal being treated, more preferably in a quantity in the range of 0.1 to 10 mg of preparation per kg body weight of the mammal being treated and even more preferably in quantity in the range of 0.1 to 1 mg of preparation per kg body weight of the mammal being treated. According to the invention it is also possible to indicate the quantities as quantities of the preparation per surface of the body of the mammal being treated. In this case, in preferred embodiments of the invention, the quantities are 0.1 to 500 mg of the preparation per 50 to 250 $cm^2$ body surface of the mammal being treated, more preferably 0.1 to 100 mg preparation per 10 to 50 $cm^2$ body surface, even more preferably 0.1 to 5 mg preparation per 4 to 10 $cm^2$ body surface of the mammal being treated.

The treatment can—as disclosed above—be repeated once or several times in the same quantities or in quantities that differ slightly from said quantities.

The invention will be described in more detail by the following examples. The examples are only used for exemplary illustration of the invention however and do not serve to restrict it.

EXAMPLES

A TCR transgenic mouse model was used to prove successful implementation of the method according to the invention and the usefulness of the pharmaceutical preparations of the present invention. In this model a defined transgenic, which codes for a specific T cell receptor that recognises a specific MHC class I ligand (SGPSNTPPEI (SEQ ID NO: 23); abbreviated to SGP) from the adenovirus type 5 in the context of MHC class I (H2-D$^b$), was introduced into mice. As already characterised by the inventors ["M. Hofmann, M. Radask, G. Rechtsteiner, K. Wiemann, M. Grander, U. Bien-Gräter, R. Offfringa, R.E.M. Toes, H.G. Rammensee, H. Schild; T cell avidity determines the level of CTL activation; Eur. J. Immunol. 2004: 34, 1798 to 1806"], the cytotoxic T cells (CTL) from these animals were only activated if they came into contact with this MHC class I ligand SGP in the context of H2-D$^b$. To be able to follow the activation of this CTL in the recipient animal the non-activated (naïve) CTL from transgenic donor mice was intravenously (i.v.) injected into syngenic recipient mice which differed in the allele of a lymphocyte marker (CD45.1 on transgenic cells or CD45.2 on cells of the recipient mice). Activation or expansion of the specific (CD45.1-positive) CTL can thus be followed following immunisation treatment.

Animals and materials

The following mice were used:
ST35-C57BL/6 (TCR transgenic mouse strain which recognises the peptide SGPSNTPPEI (SEQ ID NO: 23) (abbreviated to SGP) on D$^b$; RAG2$^{-/-}$; CD45.1; self-bred);
Recipient animals: C57BL/6; origin: ZVTE University of Mainz.

An imiquimod-containing cream (Aldara® 5%, 3M) was used for transcutaneous immunisations.

The peptide SGPSNTPPEI (SEQ ID NO: 23) from the E1A protein of adenovirus type 5 was synthetically produced by PD Dr. Stefan Stevanovic, Institute for Cell Biology, Department of Immunology, University of Tübingen.

The following monoclonal antibodies were used: anti-CD8 APC-Cy7-conjugated, anti-CD45.1 PE-conjugated (commercially available from Becton-Dickinson Pharmingen, Hamburg).

Preparation of Spleen Cells

Mice were killed; the spleen was removed, mixed with 5 ml phosphate-buffered saline (PBS) and squashed using the plunger of a 5 ml syringe in a 70 μm nylon screen over a 50 ml tube. The cells were flushed into the tube with another 5 ml PBS and centrifuged off (1500 rpm, 3 min). To remove the erythrocytes the cell pellet was resuspended in 5 ml ice cold ACK buffer (150 mM NH$_4$Cl; 1 mM KHCO$_3$; 0.1 mM EDTA; pH 7.3) and incubated for 5 min at RT. The cells were centrifuged off and washed once with PBS. The cells were counted using a Neubauer counting chamber and resuspended in PBS at 12×10$^6$ cells per ml.

Adoptive Transfer

250 μl of the spleen suspension (corresponds to 3×10$^6$ cells) were drawn into a 1 ml syringe and stored on ice until injection. The recipient mice were place in a retention system and the cell suspension was injected intravenously into the tail vein.

Transcutaneous Immunisation

The adoptive transferred mice had their backs shaved under anaesthesia (Metofane, Janssen-Cilag), resulting in an approximately 10 cm$^2$ bald patch. For immunisation a mixture of 50 mg TLRP7 ligand ("imiquimod") cream (Aldara®, 3M) and the synthetic peptide SGP (parent solution: 10 μg/ml in DMSO) were applied to the backs of the mice. Immunisation was repeated after 24 h.

Intradermal Application of Peptide and Transcutaneous Activation of Antigen-presenting Cells The adoptive transferred mice had their backs shaved under anaesthesia (Metofane, Janssen-Cilag), resulting in an approximately 10 cm$^2$ bald patch. For immunisation the mice were firstly intradermally injected under anaesthesia with peptide (from the DMSO parent solution diluted to 250 μl in PBS). A short while later 50 mg TLR7 ligand ("imiquimod") cream (Aldara®, 3M) was applied to the backs of the mice. The application of the cream was repeated after 24 h.

Analysis of the Number of Cytotoxic T Cells (CTL) in Blood

To measure the proliferation of the adoptively transferred cells blood was taken from the tail vein of the mice 4 days after the last immunisation and the blood sample was analysed flow cytometrically. For this purpose the erythrocytes were first of all lysed in ACK buffer. The residual cells were taken up in FACS buffer (0.5% bovine serum albumin (BSA), 2 mM EDTA, sodium azide in PBS) and washed once in FACS buffer. For flow cytometric analysis of the cells they were stained with fluorescence-marked antibodies (anti-CD8 APC-Cy7-conjugated, anti-CD45.1 PE-conjugated (commercially available from Becton-Dickinson Pharmingen, Hamburg)) and, more precisely, for 30 min in 50 μl FACS buffer on ice in 96-well circular bottomed plates. The cells were washed twice with FACS buffer and analysed in a FACS-canto flow cytometer (Becton-Dickinson Pharmingen, Hamburg). The CD8-positive blood lymphocytes were investigated with regard to the CD54.1-positive cell content.

In Vivo Killer Assay

The specific cytotoxic functionality of the activated cells was determined by means of what is known as an in vivo killer assays 6 days after the last immunisation. For this purpose spleen cells marked with CFSE (5,6-carboxyfluorescein diacetate succinimidylester, Molecular Probes) from syngenic mice were used as target cells for the cytotoxic T cells (CTLs). Half of the cells were dyed with 3 μM CFSE, the other half with 0.3 μM CFSE. The cells marked with 3 μM CFSE were charged with the synthetic SGP peptide (10 μM peptide; 40×10$^6$ cells per ml ISC medium; 1 h; 37° C.) and these were then washed twice with medium and twice with PBS. The cells marked with 0.3 μM CFSE were only incubated in ISC medium and also washed. The cells were mixed in a ratio of 1:1 and the mice were injected in vivo with 15×10$^6$ cells in 300 μl PBS in each case. After 18 h the mice were killed and the spleen cells removed and flow cytometrically analysed. The CFSE-positive cells were counted in a FACS-Canto flow cytometer. The specific lysis resulted from the ratio of cell counts of the cells charged with peptide and strongly marked with CFSE and the cells that were not charged with peptide and were weakly marked with CFSE. Since the two cell populations had been used in a ratio of 1:1 the number of cells not charged with peptide tallies with the original number of cells charged with peptide. The specific lysis is then calculated as follows:

$$\text{Specific lysis [\%]} = \frac{(\text{Number of cells without peptide} - \text{number of cells with peptide})}{(\text{Number of cells without peptide})}$$

CFSE Marking

The spleen cells were prepared as described above. Following ACK lysis the cells were resuspended in 10 ml PBS, counted and adjusted to 2×10$^7$ cells per ml. The cell suspension was mixed with an adequate volume of a 6 μM or 0.6 μM CFSE solution (in PBS) and incubated for 4 min at 37° C. The reaction was then stopped following addition of double the volume of ISC medium supplemented with 10% foetal calf serum (FCS). The cells were washed twice with FCS-free medium and counted.

Results

Figure 1:
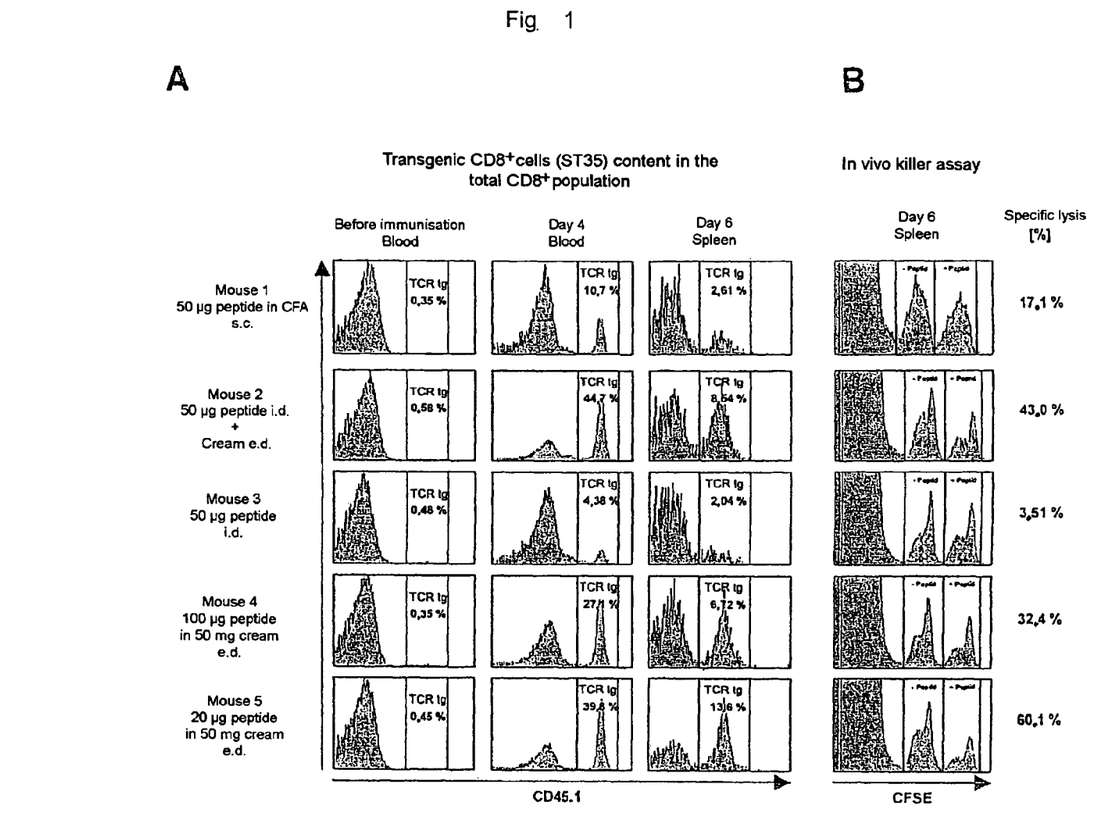
FIG. 1A represents the proliferation of transcutaneously activated transgenic cytotoxic T cells in mice.
FIG. 1B represents the functionality of transcutaneously activated transgenic cytotoxic T cells in mice.

To prove the functional principle of transcutaneous immunisation in the test TCR transgenic cytotoxic T cells (CTL) were injected i.v. into congenic recipient mice and these were immunised with their specific MHC class I ligand. The results are shown in FIG. 1 (FIG. 1: Proliferation (A) and Functionality (B) of transcutaneously activated transgenic cytotoxic T cells).

The transgenic $CD8^+$ cell content in the total population of $CD8^+$ cells was flow cytometrically determined in the blood or spleen. For this purpose the lymphocytes were stained with the antibodies anti-CD8 APC-Cy7-conjugated, anti-CD45.1 PE-conjugated (commercially available from Becton-Dickinson Pharmingen, Hamburg). The fluorescence in the FL-2 channel (PE) of the $CD8^+$ lymphocytes can be seen in each case. The $CD45.1^+$ cells content is given in percent in the respective histograms. In all mice the transgenic $CD8^+$ cells content prior to immunisation and 4 days after immunisation was determined in the spleen (A).

To determine the functionality of the activated cells an in vivo killer assay was carried out 6 days after immunisation. For this purpose syngenic spleen cells marked with a high CFSE concentration were charged with peptide, mixed 1:1 with cells marked with a weak CFSE concentration and not charged with peptide and transferred i.v. into the mice. After 18 h the spleens of the mice were removed and the number of the two cell populations marked with CFSE compared. A reduction in the number of cells charged with peptide demonstrated a specific lysis of the activated CTLs. The fluorescence of the spleen cells in the FL-1 channel (CFSE) can be seen in each case. The lysis was calculated to the number of uncharged cells and is given in percent (B).

As is clear from FIG. 1 all animals had substantially the same transgenic CTL content in their blood before immunisation (<0.6% of $CD8^+$ CTL, FIG. 1A, left-hand row). After immunisation according to the conventional protocol (peptide with complete Freund's adjuvans, CFA) the animal's transgenic CTL content increased to approx. 10% on day 4. Compared therewith a much higher specific CTL content could be observed after intradermal (i.d.) peptide application and epidermal application of Toll-like receptor ligand (imiquimod; Aldara® cream) (44.7%) or epidermal application of peptide+imiquimod (up to 39.8%). If, on the other hand, the peptide is applied on its own (without additives, adjuvants), only a marginal increase in transgenic cells took place. On day 6 these activated CTLs could also be detected in the spleen as a lymphoidal organ. This points to the fact that symmetrical activation of the CTL took place, and this shows that for the activation of the TCR transgenic CTL an adjuvant (CFA, imiquimod) is still required in addition to the specific peptide. The results show that the local application of a Toll-like receptor ligand such as imiquimod is superior to conventional immunisation with CFA as far as the expansion of the specific cytotoxic T cells is concerned.

FIG. 1B shows that the expansion of the transgenic CTL is also accompanied by functional activity. Transferred target cells which had been marked with peptide were specifically destroyed while unmarked cells were not destroyed (specific lysis). The efficiency of the specific lysis is dependent on prior activation of the transgenic CTL. As illustrated the group "Mouse 1", which was immunised with CFA, shows only a specific lysis of approx. 17%, while optimally activated CFL specifically lyse a content of approx. 60%. If immunisation is with peptide only (group "Mouse 3") this does not lead to functional activation of the CTL.

The results can also be found in Table 2 below.

TABLE 2

Results of the immunisation test
% transgenic $CD8^+$ in total $CD8^+$

| Group mouse no. | Before immunisation | Day 4 Blood | Day 6 Spleen | Specific lysis (%) |
|---|---|---|---|---|
| 1 | 0.35 | 10.66 | 2.61 | 17.05 |
| 2 | 0.58 | 44.66 | 8.54 | 43.04 |
| 3 | 0.48 | 4.38 | 2.04 | 3.51 |
| 4 | 0.35 | 27.05 | 6.72 | 32.36 |
| 5 | 0.45 | 39.75 | 13.63 | 60.05 |

Notes:
The specific lysis values were determined by means of an in vivo killer assay.
Treatment: Group no. 1: 50 µg peptide + CFA (s.c.)
Group no. 2: 50 µg peptide (i.d.) + imiquimod cream (e.d.)
Group no. 3: 50 µg peptide (i.d.)
Group no. 4: 100 µg peptide + imiquimod cream (e.d.)
Group no. 5: 20 µg peptide + imiquimod cream (e.d.)

Figure 2:
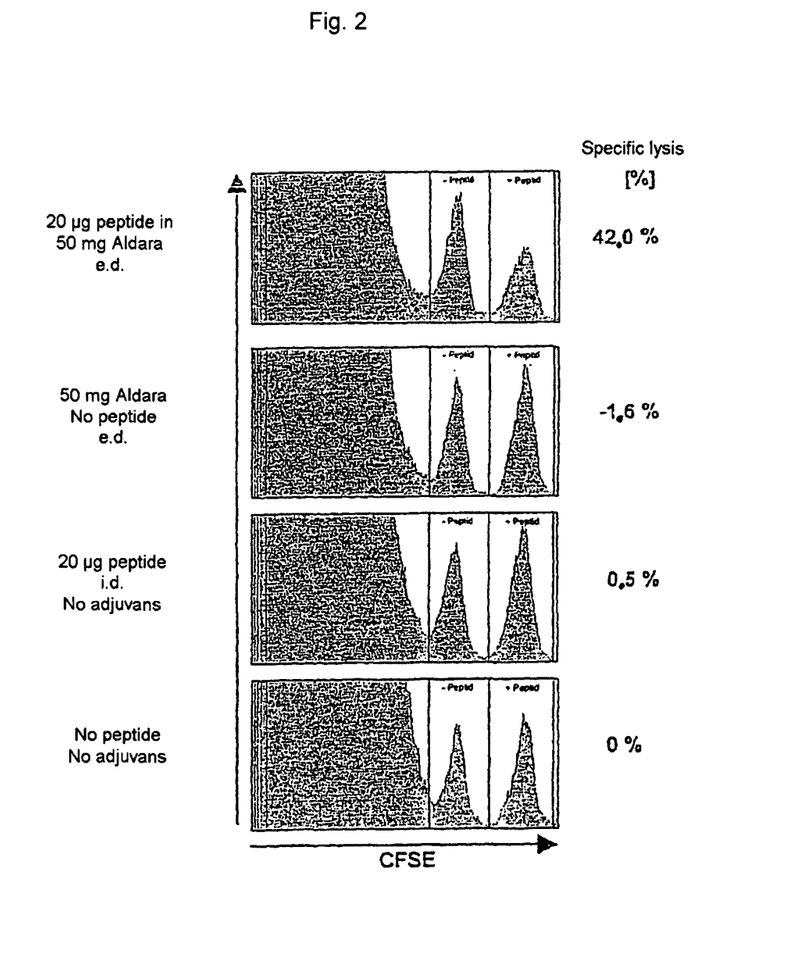
FIG. 2 also represents the functionality of transcutaneously activated transgenic cytotoxic T cells in mice.

To show that the activation of CTL is dependent on the presence of the specific peptide and the additional activation by the TLR ligand (imiquimod), transgenic CTL was transferred into recipient mice and these were treated with the preparation containing the TLR ligand (imiquimod) which contained the peptide or did not contain it. As shown in FIG. 2 ("Functionality of transcutaneously activated cytotoxic T cells), only the group of mice which were treated with the preparation containing the peptide and the TLR ligand together exhibited a specific reaction while the animals which were not treated, or which were treated with preparations which contained each of the active ingredients on their own, did not exhibit a specific reaction. This test shows that both components are imperative for activation of the cytotoxic T cells to be achieved by transcutaneous immunisation.

FIG. 2 shows the functionality of transcutaneously activated transgenic cytotoxic T cells. To determine the functionality of the activated cells an in vivo killer assay was carried out 6 days after immunisation. For this purpose syngenic spleen cells marked with a high CFSE concentration were charged with peptide, mixed in a ratio of 1:1 with cells marked with a weak CFSE concentration and not charged with peptide and transferred i.v. into the mice. After 18 h the spleens of the mice were removed and the number of the two cell populations marked with CFSE compared. A reduction in the number of cells charged with peptide demonstrated a specific lysis of the activated CTLs. The fluorescence of the spleen cells in the FL-1 channel (CFSE) can be seen in each case. The specific lysis was calculated to the number of uncharged cells and is given in percent.

The pharmaceutical preparations according to the invention and their use as well as the method according to the invention show that it is possible to activate antigen-specific cytotoxic T cells which are then also functional. Requirements for the functionality are firstly the presence of APC in the skin, which can present a MCH class I ligand, and secondly knowledge about the exact structure of the MCH molecules and the antigen against which immunisation is to be carried out. No injections are required for the new vaccination method, and this significantly simplifies the method and pharmaceutical preparations for its use are significantly less expensive.

The present invention therefore relates to a pharmaceutical preparation comprising at least one Toll-like receptor ligand, at least one peptide and optionally one or more substance(s) from the group comprising carriers, adjuvants and additives.

In a preferred embodiment the invention relates to a pharmaceutical preparation according to the above definition with the at least one Toll-like receptor ligand being selected from the group comprising TLR2 ligand, TLR3 ligand, TLR7 ligand, TLR8 ligand and TLR9 ligand, preferably with the at least one Toll-like receptor ligand being a TLR7 ligand.

A further preferred embodiment of the invention relates to a pharmaceutical preparation according to the above definition with the at least one Toll-like receptor ligand being selected from the group comprising compounds of natural and/or synthetic origin which are recognised by at least one Toll-like receptor ligand and are useful for triggering one or more signal(s) that promote the immune response, preferably with the at least one Toll-like receptor ligand being selected from the group comprising Pam3Cys, poly-(I:C), imiquimod, loxoribine, R-848 and CpG-DNA, even more preferably with the Toll-like receptor ligand being imiquimod.

A further preferred embodiment of the invention relates to a pharmaceutical preparation according to one of the above definitions, with the at least one peptide being selected from the major histocompatibility complex class I ligand, major histocompatibility complex class II ligand and further peptides containing these ligands.

A further preferred embodiment of the invention relates to a pharmaceutical preparation according to one of the above definitions comprising at least one Toll-like receptor ligand in a quantity of 0.1 to 10% by weight, at least one peptide in a quantity of 0.01 to 30% by weight and one or more substance(s) from the group comprising carriers, adjuvants and additives in a total quantity of 0.1 to 99.9% by weight, in each case based on the total weight of the pharmaceutical preparation.

A further preferred embodiment of the invention relates to a pharmaceutical preparation according to one of the above definitions comprising the at least one synthetic Toll-like receptor ligand and the at least one synthetic peptide in a formulation for combined administration and effect.

A further preferred embodiment of the invention relates to a pharmaceutical preparation according to one of the above definitions comprising the at least one synthetic Toll-like receptor ligand and the at least one synthetic peptide in separate formulations for separate administration and combined effect.

A further preferred embodiment of the invention relates to a pharmaceutical preparation according to one of the above definitions in a formulation that is suitable for topical administration.

A further preferred embodiment of the invention relates to a pharmaceutical preparation according to one of the above definitions in a formulation that is suitable for topical administration of one component and for non-topical, preferably subcutaneous or intradermal, administration of another component with the aim of a combined effect.

A further preferred embodiment of the invention relates to a pharmaceutical preparation according to the above definition in a formulation suitable for the topical administration of at least one Toll-like receptor ligand and a formulation for the non-topical, preferably subcutaneous or intradermal, administration of at least one synthetic peptide with the aim of a combined effect.

The present invention also relates to the use of a pharmaceutical preparation according to one of the above definitions for the prophylaxis and/or therapy of diseases in a mammal induced by viruses and/or bacteria and/or fungi.

The present invention also relates to the use of a pharmaceutical preparation according to one of the above definitions for the prophylaxis and/or therapy of diseases in a mammal caused by excessive cell proliferation.

The present invention also relates to the use of a pharmaceutical preparation according to one of the above definitions for the preparation of a pharmaceutical composition for the prophylaxis and/or therapy of diseases in a mammal induced by viruses and/or bacteria and/or fungi.

The present invention also relates to the use of a pharmaceutical preparation according to one of the above definitions for the preparation of a pharmaceutical composition for the prophylaxis and/or therapy of diseases in a mammal caused by excessive cell proliferation.

A preferred embodiment of the invention relates to the use according to one of the above definitions with the mammal being a human.

A further preferred embodiment of the invention relates to the use according to one of the above definitions by way of topical application of the pharmaceutical preparation, preferably by way of application of the pharmaceutical preparation to the skin of the mammal.

A further preferred embodiment of the invention relates to the use according to one of the above definitions by way of separate topical application of one component and non-topical, preferably subcutaneous or intradermal, application of another component with the aim of a combined effect, preferably by way of topical application of one component to the skin of the mammal and subcutaneous or intradermal application of another component immediately before or after or at the same time as the topical application.

A further preferred embodiment of the invention relates to the use according to the above definition by way of separate topical application of a formulation comprising at least one Toll-like receptor ligand and subcutaneous or intradermal application of a formulation comprising at least one synthetic peptide with the aim of a combined effect.

The present invention also relates to a method for the prophylaxis and/or therapy of diseases in a mammal induced by viruses and/or bacteria and/or fungi, comprising the administration of a pharmaceutical preparation, according to one of the above definitions, to the mammal in a concentration of the pharmacologically effective components that is effective for the prophylaxis and/or therapy of said diseases.

The present invention also relates to a method for the prophylaxis and/or therapy of diseases in a mammal caused by excessive cell proliferation, comprising the administration of a pharmaceutical preparation, according to one of the above definitions, to the mammal in a concentration of the pharmacologically effective components that is effective for the prophylaxis and/or therapy of said diseases.

The present invention also relates to a method for the prophylactic and/or therapeutic activation of the adaptive immune system of a mammal, comprising the administration of a pharmaceutical preparation, according to one of the above definitions, to the mammal in a concentration of the pharmacologically effective components that is effective for the prophylactic and/or therapeutic activation of the immune system.

The present invention also relates to a method for the prophylactic and/or therapeutic activation of cytotoxic T cells in the immune system of a mammal, comprising the administration of a pharmaceutical preparation, according to one of the above definitions, to the mammal in a concentration of the pharmacologically effective components that is effective for the prophylactic and/or therapeutic activation of the cytotoxic T cells.

A preferred embodiment of the invention relates to a method according to one of the above definitions with the mammal being a human.

A further preferred embodiment of the invention relates to a method according to one of the above definitions with the pharmaceutical preparation being administered topically, preferably with the pharmaceutical preparation being applied to the skin of the mammal.

A further preferred embodiment of the invention relates to a method according to one of the above definitions with part of the pharmaceutical preparation comprising one component being administered topically and another part of the pharmaceutical preparation comprising another component being administered non-topically, preferably subcutaneously or intradermally, with the aim of a combined effect, more preferably with part of the pharmaceutical preparation comprising one component being administered by application to the skin of the mammal and administration of another part of the pharmaceutical preparation comprising another component being brought about by subcutaneous or intradermal administration to the mammal immediately before or after or at the same time as application to the skin with the aim of a combined effect.

In a further preferred embodiment the invention relates to a method according to the above definition with part of the preparation, comprising at least one Toll-like receptor ligand, being administered by way of topical application to the skin and another part of the preparation, comprising at least one peptide, being administered subcutaneously or intradermally.

What is claimed is:

1. A pharmaceutical preparation which comprises from 0.1% to 10% by weight of (a) at least one Toll-like receptor ligand selected from TLR7 ligands, from 0.01% to 30% by weight of (b) at least one peptide selected from (i) major histocompatibility complex class I ligands, (ii) major histocompatibility complex class II ligands, and (iii) peptides which comprise one or more of these histocompatibility complex ligands and are capable of being presented by at least one of a MHC class I molecule and a MHC class II molecule, and from 0.1% to 99.9% by weight of (c) one or more substances selected from carriers, adjuvants and additives, in each case based on a total weight of the preparation; wherein said pharmaceutical preparation elicits increased T cell mediated immune response compared to peptide (b) alone.

2. The preparation of claim 1, wherein the at least one Toll-like receptor ligand comprises imiquimod.

3. The preparation of claim 1, wherein the at least one Toll-like receptor ligand comprises loxoribine.

4. The preparation of claim 1, wherein the at least one Toll-like receptor ligand comprises R-848.

5. The preparation of claim 1, wherein at least one of (a) and (b) is either a fully synthetic compound or a synthetically modified naturally occurring compound.

6. The preparation of claim 1, wherein the preparation comprises from 1% to 5% by weight of (a) and from 0.2% to 2% by weight of (b).

7. The preparation of claim 1, wherein the preparation is present in a form which is suitable for topical administration.

8. A method for the prophylaxis and/or therapy in a mammal of a disease which is induced by at least one of viruses, bacteria and fungi, wherein the method comprises administering to the mammal the pharmaceutical preparation of claim 1 in an amount which is effective for the prophylaxis and/or therapy of the disease.

9. A method for the prophylaxis and/or therapy in a mammal of a disease which is caused by excessive cell proliferation, wherein the method comprises administering to the mammal the pharmaceutical preparation of claim 1 in an amount which is effective for the prophylaxis and/or therapy of the disease.

10. A method for the prophylactic and/or therapeutic activation of the adaptive immune system of a mammal, wherein the method comprises administering to the mammal the pharmaceutical preparation of claim 1 in an amount which is effective for the prophylactic and/or therapeutic activation of the mammal's immune system.

11. A method for the prophylactic and/or therapeutic activation of cytotoxic T cells in an immune system of a mammal, wherein the method comprises administering to the mammal the pharmaceutical preparation of claim 1 in an amount which is effective for the prophylactic and/or therapeutic activation of the cytotoxic T cells.

12. A pharmaceutical preparation which is suitable for topical administration and comprises from 1% to 5% by weight of (a) at least one Toll-like receptor ligand selected from imiquimod, loxoribine, and R-848, from 0.2% to 2% by weight of (b) at least one peptide selected from (i) major histocompatibility complex class I ligands, (ii) major histocompatibility complex class II ligands, and (iii) peptides which comprise one or more of these histocompatibility complex ligands and are capable of being presented by at least one of a MHC class I molecule and a MHC class II molecule, and up to 98.8% by weight of (c) one or more substances selected from carriers, adjuvants and additives, in each case based on a total weight of the preparation.

13. A pharmaceutical combination, wherein the combination comprises (a) at least one Toll-like receptor ligand selected from TLR7 ligands and (b) at least one peptide selected from (i) major histocompatibility complex class I ligands, (ii) major histocompatibility complex class II ligands, and (iii) peptides which comprise one or more of these histocompatibility complex ligands and are capable of being presented by at least one of a MHC class I molecule and a MHC class II molecule, (a) and (b) being present in at least two separate formulations wherein said pharmaceutical combination elicits increased T cell mediated immune response compared to peptide (b) alone.

14. The combination of claim 13, wherein the at least one Toll-like receptor ligand is selected from compounds of synthetic origin which are capable of being recognized by at least one Toll-like receptor and are capable of contributing to a triggering of one or more signals which promote an immune response.

15. The combination of claim 13, wherein the at least one Toll-like receptor ligand comprises imiquimod.

16. The combination of claim 13, wherein the at least one Toll-like receptor ligand comprises loxoribine and/or R-848.

17. The combination of claim 13, wherein at least one of (a) and (b) is either a fully synthetic compound or a synthetically modified naturally occurring compound.

18. The combination of claim 13, wherein a first one of the at least two separate formulations is present in a form which is adapted for topical administration and a second one of the at least two formulations is present in a form which is adapted for non-topical administration.

19. The combination of claim 18, wherein the second one of the at least two formulations is present in a form which is adapted for at least one of a subcutaneous and an intradermal administration.

20. The combination of claim 18, wherein the first one of the at least two formulations comprises (a) and the second one of the at least two formulations comprises (b).

21. A method for the prophylaxis and/or therapy in a mammal of a disease which is induced by at least one of viruses, bacteria and fungi, wherein the method comprises administering to the mammal the pharmaceutical combination of claim 13 in an amount which is effective for the prophylaxis and/or therapy of the disease.

22. A method for the prophylaxis and/or therapy in a mammal of a disease which is caused by excessive cell proliferation, wherein the method comprises administering to the mammal the pharmaceutical combination of claim 13 in an amount which is effective for the prophylaxis and/or therapy of the disease.

23. A method for the prophylactic and/or therapeutic activation of the adaptive immune system of a mammal, wherein the method comprises administering to the mammal the pharmaceutical combination of claim 13 in an amount which is effective for the prophylactic and/or therapeutic activation of the mammal's immune system.

24. A method for the prophylactic and/or therapeutic activation of cytotoxic T cells in an immune system of a mammal, wherein the method comprises administering to the mammal the pharmaceutical combination of claim 13 in an amount which is effective for the prophylactic and/or therapeutic activation of the cytotoxic T cells.

* * * * *